(12) United States Patent
Oberwalder et al.

(10) Patent No.: US 10,315,937 B2
(45) Date of Patent: Jun. 11, 2019

(54) APPARATUS FOR GERM REDUCTION OF A FLUID AND A PROCESS FOR USE THEREOF

(71) Applicant: Sulzer Chemtech AG, Winterthur (CH)

(72) Inventors: Hanns Wolf Oberwalder, Salzburg (AT); Sebastian Oberwalder, München (DE); Thomas Müller, Baar (CH); Marc Wehrli, Brütten (CH); Sebastian Hirschberg, Winterthur (CH)

(73) Assignee: Sulzer Chemtech AG, Winterthur (CH)

( * ) Notice: Subject to any disclaimer, the term of this patent is extended or adjusted under 35 U.S.C. 154(b) by 385 days.

(21) Appl. No.: 14/888,498

(22) PCT Filed: May 6, 2014

(86) PCT No.: PCT/EP2014/059144
§ 371 (c)(1),
(2) Date: Nov. 2, 2015

(87) PCT Pub. No.: WO2014/180799
PCT Pub. Date: Nov. 13, 2014

(65) Prior Publication Data
US 2016/0052806 A1    Feb. 25, 2016

(30) Foreign Application Priority Data
May 8, 2013  (EP) ..................... 13166965

(51) Int. Cl.
*A01N 25/10*  (2006.01)
*A01N 25/34*  (2006.01)
(Continued)

(52) U.S. Cl.
CPC ............... *C02F 1/50* (2013.01); *A01N 25/10* (2013.01); *A01N 25/34* (2013.01); *A61L 2/232* (2013.01);
(Continued)

(58) Field of Classification Search
CPC .......... C02F 1/50; C02F 1/685; B01F 5/0602; B01F 5/0615; B01F 5/0619; B01F 5/0695;
(Continued)

(56) References Cited

U.S. PATENT DOCUMENTS 3,918,688 A   11/1975  Huber et al.
5,688,047 A   11/1997  Signer
(Continued)

FOREIGN PATENT DOCUMENTS

CN   102369944 A    3/2012
DE   29521609 U1    11/1997
(Continued)

OTHER PUBLICATIONS

"Water: Density, Viscosity, Specific Weight," EngineersEdge.com (2018).*

(Continued)

*Primary Examiner* — Lucas A Stelling
(74) *Attorney, Agent, or Firm* — Larson & Anderson, LLC

(57) ABSTRACT

A static devolatilization apparatus (1) for germ reduction of a fluid is disclosed. The apparatus (1) comprises a housing (10), an inlet (12), an outlet (14), a fluid-contacting surface (20) comprising a biocide (22) embodied to reduce the germ count of the fluid (2), wherein the fluid-contacting surface (20) is a fluid-contacting surface (20) of a static mixing element (30). The present invention further relates to a process for reducing the germ count of a fluid containing germs (2') using the apparatus (1) and also to the use of the apparatus (1) in the germ reduction of fuel oil, of food products, or water decontamination, preferably decontamination of waste water, industrial process water, or the treatment of drinking water.

19 Claims, 9 Drawing Sheets

(51) Int. Cl.
  *A61L 2/232* (2006.01)
  *B01F 5/06* (2006.01)
  *C02F 1/50* (2006.01)
  *C02F 1/68* (2006.01)
  *B01F 5/00* (2006.01)

(52) U.S. Cl.
  CPC .......... *B01F 5/0602* (2013.01); *B01F 5/0615* (2013.01); *B01F 5/0619* (2013.01); *B01F 5/0695* (2013.01); *B01F 2005/0097* (2013.01); *C02F 1/685* (2013.01)

(58) Field of Classification Search
  CPC . B01F 2005/0097; A01N 25/10; A01N 25/34; A61L 2/232
  See application file for complete search history.

(56) References Cited

U.S. PATENT DOCUMENTS

| | | |
|---|---|---|
| 6,053,368 A | 4/2000 | Geimer |
| 6,206,349 B1 | 3/2001 | Parten |
| 6,501,079 B1 | 12/2002 | Furuya |
| 7,819,140 B2 | 10/2010 | Bass et al. |
| 2003/0078242 A1* | 4/2003 | Raad ...................... A01N 31/12 514/150 |
| 2006/0231470 A1* | 10/2006 | Hatch ...................... C02F 1/725 210/198.1 |
| 2010/0118642 A1 | 5/2010 | Ho et al. |

FOREIGN PATENT DOCUMENTS

| | | |
|---|---|---|
| EP | 0697374 A1 | 2/1996 |
| EP | 2338342 A1 | 6/2011 |
| EP | 2338923 A1 | 6/2011 |
| GB | 1373142 A | 11/1974 |
| GB | 2061746 A | 5/1981 |
| JP | H04-22092 U | 2/1992 |
| JP | 2006-230929 A | 9/2006 |
| JP | 2009-291284 A | 12/2009 |
| WO | 2004/052961 A1 | 6/2004 |

OTHER PUBLICATIONS

Machine translation of EP 2338342 A1 to Oberwalder et al., 2009 (obtained from Google Patents 2018) (Year: 2009).*
Machine translation of EP 233923 A1 to Oberwalder et al., 2009 (obtained from Google Patents 2018) (Year: 2009).*

* cited by examiner

1. General formula for Polymeric Guanidines (A)

(A)

(A)

APPARATUS FOR GERM REDUCTION OF A FLUID AND A PROCESS FOR USE THEREOF

BACKGROUND OF THE INVENTION

The present invention relates to an apparatus for germ reduction of a fluid. The present invention also relates to a process for using said apparatus for reducing the germ count of a fluid containing germs and the use of said apparatus for germ reduction of fuel oil, of food products, or water decontamination, preferably decontamination of waste water, industrial process water, or the treatment of drinking water.

Germ reduction of fluids is of widespread commercial interest, for example, for sanitation, hygiene and drinking water purposes and in the medical and food industries. The term "germ" in the present application is not specifically limited and it is defined as a microorganism, particularly pathogenic or spoilage ones.

Various types of apparatuses for germ reduction of fluids are known, and they are generally based on filtering apparatuses. For example, WO 2004/052961 A1 discloses a variety of such filtering apparatuses making use of special guanidine copolymers as the germ-reducing material. These copolymers, however are disclosed in the form of either water soluble or gel materials only. It is noted that water soluble or gel materials are not stable materials for construction of devices and their components. Water soluble or gel materials generally also do not have long-term stability when exposed to fluids, and, for example, they may deform or lose their active components. It is generally undesirable for the potentially toxic water-soluble biocide materials of the prior art to leach out of the apparatus and its components due environmental, health and safety and (other) regulatory aspects.

In the disclosed filtering apparatuses the guanidine copolymer is in the form of a granulate, powder or gel and packed into a filtration column through which the fluid to be treated is then passed. Alternatively it is disclosed that the guanidine copolymer may be coated onto a paper, cellulose or fabric material, which is then used as a filtering element in the apparatus. Filtration devices suffer from the disadvantage that their use entails significant pressure drops. These pressure drops result from their limited void fraction and high specific surface—both of which are used to achieve a high interfacial contact between the fluid and the solid phase.

Although guanidine based polymers are effective in germ reduction, they—like most germ-reduction materials—are not yet a commodity material, and thus they are still relatively expensive specialty polymers only available in limited production volumes from specialty polymer producers. The relatively high cost of such germ-reducing materials (biocides) then results in a drawback of such known filtering apparatuses for germ reduction. Such filtering devices generally require the use of relatively large quantities of expensive germ-reducing material. This is because filter columns typically have only relatively small void fractions for contact of the fluid to be treated with the biocide, and thus they require longer columns or lower flow rates for a particular specific surface area in order to generate sufficient residence time to be effective. Furthermore limitations to the usable specific surface area arise due to pressure drop considerations.

In addition, in the case of filtering apparatuses making use of columns of biocide in the form of granulate, powder or gel, as in WO 2004/052961, a very large fraction of the biocide is "wasted", as only the outer surface of the granulate, powder or gel contacts the fluid and is effective. The bulk of the biocide in the interior of the granulate, powder or gel is thus inactive due to a lack of contact with the fluid.

In conclusion, it would be desirable to have an apparatus for germ reduction of a fluid which makes more efficient use of expensive specialty biocide materials. Such an apparatus would allow for a more efficient germ reduction for a given quantity of biocide. It would furthermore be desirable if said apparatus did not suffer from the disadvantages of high pressure drops or lack of long-term stability upon exposure to fluids, such as due to leaching out of the biocide. Furthermore it would be preferred if the germ reduction could be improved even still further relative to that of the state of the art filtering apparatuses.

SUMMARY OF THE INVENTION

Starting from this state of the art, it is an object of the invention to provide an apparatus for germ reduction of a fluid that does not suffer from the previous mentioned deficiencies, particularly a less efficient use of biocide materials and less effective germ reduction. Further objects of the invention include providing a process for using said apparatus for reducing the germ count of a fluid containing germs and a use of said apparatus for germ reduction of fuel oil, of food products, or water decontamination, preferably decontamination of waste water, industrial process water, or the treatment of drinking water.

According to the invention, these objects are achieved by an apparatus for germ reduction of a fluid comprising: a housing, an inlet, an outlet, a fluid-contacting surface comprising a biocide embodied to reduce the germ count of the fluid, characterized in that the fluid-contacting surface is a fluid-contacting surface of a static mixing element.

According to the invention, these further objects are achieved firstly by a process for reducing the germ count of a fluid containing germs using the apparatus of the invention comprising the steps of:

feeding the fluid containing germs to the apparatus via the inlet treating the fluid containing germs on a fluid-contacting surface comprising a biocide in order to form a fluid having a reduced germ count removing the fluid having a reduced germ count from the apparatus via the outlet.

Said apparatus and said process is used in accordance with the invention for germ reduction of fuel oil, of food products, or water decontamination, preferably decontamination of waste water, industrial process water, or the treatment of drinking water. In the present application "fuel oil" refers to all oils capable of being used as a fuel, such as diesel, gasoline or crude oil. As will be discussed, such fluids and processes particularly benefit from the present invention.

The present invention achieves these objects and provides a solution to this problem in that the fluid-contacting surface comprising a biocide embodied to reduce the germ count of the fluid is a fluid-contacting surface of a static mixing element. As a result, both the pressure loss and the amount of biocide material used are much smaller for the case of a static mixer element versus a filter such as a packed bed of granulates. This reduction in the required amount of biocide material is especially significant when only the surface of the static mixer element is coated with the biocide material. As will be shown by the examples of the invention and their comparison with state of the art filtering apparatuses, the beneficial reduction in germ count is greater for the apparatus of the invention. Furthermore the apparatus of the invention has demonstrated a good stability against loss of biocide to the fluid phase by means of leaching out of the static mixer element. This result is quite surprising and demonstrates that the apparatus and process of the invention not only makes more efficient use of expensive specialty biocide materials and thus allows for a more efficient germ reduction for a given quantity of biocide, but also that the germ reduction could be improved relative to that of the state of the art filtering apparatuses.

One skilled in the art will understand that a "fluid-contacting surface" means a surface region comprising or containing the biocide and capable of interacting with the fluid. Thus this surface region will have a depth associated with it that will vary somewhat depending on the specific nature of the interaction of the fluid and the surface due to such factors as swelling or porosity, as well as the size of the biocide molecule. In some embodiments, the depth of the surface region will depend on the particular spectroscopic method used to characterize the composition of the surface such as X-ray photoelectron spectroscopy (XPS) or Auger-electron spectroscopy (AES). In one embodiment, the depth of the fluid-contacting surface is that characterized by conventional XPS measurements. In embodiments involving biocide-containing coatings, the depth of the surface region will depend on the coating thickness and the method of coating used. In another embodiment, the depth of the fluid-contacting surface is from 1 to 1000 microns."

In one embodiment of the apparatus or process, the fluid-contacting surface does not substantially release the biocide to the fluid. In the present application, "does not substantially release" is defined as meaning that any release is so slow and insubstantial that the biocide is not present in appreciable concentrations in the fluid treated by the apparatus. For example, the concentration of biocide in the treated fluid is preferably less than 50, more preferably less than 15, even more preferably less than 1 ppm, most preferably not detectable as determined by conventional spectroscopic or chromatographic methods. In one embodiment, the gas chromatography-mass spectrometry (GC-MS) is used, as disclosed in "Analysis of Drinking Water for Trace Organics", by C. J. Koester & R. E. Clement in Critical Reviews in Analytical Chemistry Vol. 24, Issue 4, 1993. Preferably the concentration of biocide in the treated fluid is measured under static conditions over 24 hours. This embodiment has the advantage that the apparatus functions "permanently" over its lifetime. Thus it is not necessary to replace or renew the fluid-contacting surface, which then reduces maintenance and service costs and downtime. One skilled in the art will understand that different applications, such as waste water versus drinking water, will have differing requirements as to tolerable amounts of biocide release to the fluid.

According to another embodiment of the apparatus and the process, the fluid-contacting surface comprises a guanidine or a derivative thereof. Guanidines have the general structure $(R_1R_2N)(R_3R_4N)C=N-R_5$. Guanidines and their derivatives have several advantages over other biocides. For example, they are readily available and also lower cost versus other biocides such as nanosilver. In addition, guanidines and their derivatives have very good high temperature stability. As a result, they are well-suited for use in processes for reducing the germ count of a fluid containing germs that are typically carried out at elevated temperatures. Such processes may benefit then from the synergistic effect of the biocide and elevated temperature.

According to yet another embodiment of the apparatus and the process, the fluid-contacting surface comprises a biocide-containing polymer. This embodiment has several advantages. Incorporating the biocide in a polymer composition minimizes leaching-out of the biocide during the lifetime of the apparatus and thus provides permanence of the biocidal activity. Furthermore polymers are readily thermally processed by extrusion or molding and formed into shapes such as those of static mixing elements. Alternatively polymers may be readily used as coatings of static mixing elements manufactured from other materials such as metals. Such polymer coatings maybe applied by thermal or solution methods.

In a further more specific embodiment, the biocide-containing polymer is a copolymer or preferably a polymer compound. Polymer compounds have the advantage of being simpler, cheaper and more versatile to produce than biocidal copolymers, which typically require expensive monomers that are not readily commercially available in industrial quantities. Furthermore, polymerization processes and apparatuses are more complex and require larger investments and have more EHS-concerns than compounding facilities.

According to yet another embodiment of the apparatus and the process, the static mixer element contains biocide only in a surface region encompassing the fluid-contacting surface. The provision of biocide only to a surface region beneficially reduces the amount of biocide required. In addition, biocide located below the surface region in the bulk region will not contact the fluid and will thus be ineffective in germ reduction. In the present application, the depth of the surface region is defined as being 80% or less of the total thickness of the static mixer element measured at its thinnest point. This embodiment will often be achieved through the use of coating technologies, which generally entail relatively low cost processes and the consumption of limited amounts of raw materials. Furthermore one may advantageously coat a conventional static mixer element such as one made of metals or plastics. One skilled in the art will understand that, for example, very thin metal supports may be used to provide mechanical stability for the biocide-containing coating. In such embodiments, the coating will be relatively thick with respect to the thin metal support. In other embodiments, the static mixer element may be formed by means of co-extrusion methods to give a biocide-containing surface layer on an underlying support layer.

The process of the invention has many advantages in that it works well with a wide variety of fluids. Furthermore it may therefore replace neutralization and sterilization processes in a relatively low-cost and environmentally-friendly manner. In addition when the fluid to be treated is a food or beverage product the nutritional losses with the process of the invention will be less than those with harsh conventional photochemical, thermal or chemical sterilization processes. Quite importantly the raw material costs and potential health hazards and consumer concerns related to the use of preservatives may be limited or avoided.

According to one embodiment of the process, the residence time in the apparatus is less than 600, preferably 180, more preferably 60, even more preferably 10, still more preferably 5, and most preferably 1 s. One skilled in the art will understand that different applications and/or different fluids may require the use of different residence times for an effective germ reduction. The residence time is effectively the average length of time that a portion of the fluid will remain in the apparatus. In the present application, the residence time is defined as the amount of fluid in the housing of the apparatus, divided by the flow rate of the fluid out of the outlet. If there are multiple outlets, then one uses the sum of the outflows to determine the residence time. The apparatus of the invention has the advantage of enabling relatively short residence and thus processing times due to its highly effective use of the biocide. Reducing the processing time for fluids beneficially minimizes investment and operational costs, as well as apparatus size and "footprint".

According to another embodiment of the process, the temperature of the fluid in the apparatus is between 0 and 200, preferably 10 to 100, more preferably 10 to 60, most preferably 20 to 30° C. In the present application, the temperature of the fluid in the apparatus is defined as the temperature of the fluid measured in the inlet. The highly effective use of the biocide in the present invention allows a high germ reduction to occur at relatively low temperatures. This then beneficially reduces the investment and operational costs for heating devices.

According to a further embodiment of the process, the germ content of the fluid is reduced in the process by log 0.5 to 7, preferably 2 to 6, most preferably 3 to 5. The highly effective use of the biocide in the present invention makes possible such high germ reductions in the process. In the present application, the germ content is defined as the germ content measured according to the applicable ISO method, such as ISO, 9308-1, 7899-1, 16266, 19250, 6222, 38411, and 38412 for microbiologic analysis of drink water or waste water.

In yet another embodiment of the process, the pressure of the fluid in the process is less than or equal to 100, preferably 32, more preferably 16, even more preferably 10, most preferably 6 bar. These pressures are most suitable for ready construction of the apparatus and/or its typical applications, e.g. in the treatment of drinking water. In the present application, the pressure of the fluid is defined as the pressure measured at the outlet of the apparatus.

In still another embodiment of the process, the ratio of the active surface area to the volume of the apparatus is more than 50, preferably 150, more preferably 300, most preferably 600 $m^2/m^3$. Such minimum ratios allow a beneficial high efficiency and compact size of the apparatus, and because of the relatively open structure and high void fraction of the static mixer elements according to the invention, such benefits are achievable without significant pressure losses. In the present application, the ratio of the active surface area to the volume is defined as all of the available exterior surface of the static mixer element within the working volume of the apparatus encompassing the static mixer element.

In still yet another embodiment of the process, the viscosity of the fluid is less than 1000, preferably 10, more preferably 0.1 Pa s. Such viscosities help minimize undesirable pressure losses and facilitate contact between the fluid-contacting surface of the static mixing element and the fluid to be treated. In the present application, the viscosity is defined as that measured according to the suitable ISO method, such as ISO 3104:1994 for the viscosity measurement of Transparent and opaque liquids. Further information on viscosity measurements is disclosed in "Rheology: Concepts, Methods, And Applications" by A. Y. Malkin and A. I. Isayev, published by Chem Tec Publishing, Canada in 2005 (ISBN-13: 978-1895198331).

In still yet a further embodiment of the process, the pressure loss of the fluid is less than 1, preferably 0.3, most preferably 0.1 bar. Minimizing pressure losses beneficially reduces complexity and cost of the apparatus by minimizing the various energy, pumping, mechanical strength, and safety requirements. In the present application, the pressure loss is defined as the static difference between the outlet and the inlet measured in a horizontal orientation using water under ambient conditions. Suitable pressure measurement methods include those disclosed in "Instrumentation and Control for the Chemical, Mineral, and Metallurgical Processes" by V. R. Radhakrishnan, Allied Publishers, India, 1997 (ISBN: 81-7023-723-8).

One embodiment of the process and a use of the apparatus is for germ reduction of fuel oil, of food products, or water decontamination, preferably decontamination of waste water, industrial process water, or the treatment of drinking water. The invention has proven to be particularly useful in the germ reduction of such fluids.

One skilled in the art will understand that the combination of the subject matters of the various claims and embodiments of the invention is possible without limitation to the extent that such combinations are technically feasible. In this combination, the subject matter of any one claim may be combined with the subject matter of one or more of the other claims. In this combination of subject matters, the subject matter of any one process claim may be combined with the subject matter of one or more other process claims or the subject matter of one or more apparatus claims or the subject matter of a mixture of one or more process claims and apparatus claims. By analogy, the subject matter of any one apparatus claim may be combined with the subject matter of one or more other apparatus claims or the subject matter of one or more process claims or the subject matter of a mixture of one or more process claims and apparatus claims.

One skilled in the art will understand that the combination of the subject matters of the various embodiments of the invention is possible without limitation in the invention. For example, the subject matter of one of the above-mentioned apparatus embodiments may be combined with the subject matter of one or more of the other above-mentioned process embodiments or vice versa without limitation.

BRIEF DESCRIPTION OF THE DRAWINGS

The invention will be explained in more detail hereinafter with reference to various embodiments of the invention as well as to the drawings. The schematic drawings show.

DETAILED DESCRIPTION OF THE INVENTION

Figure 1:
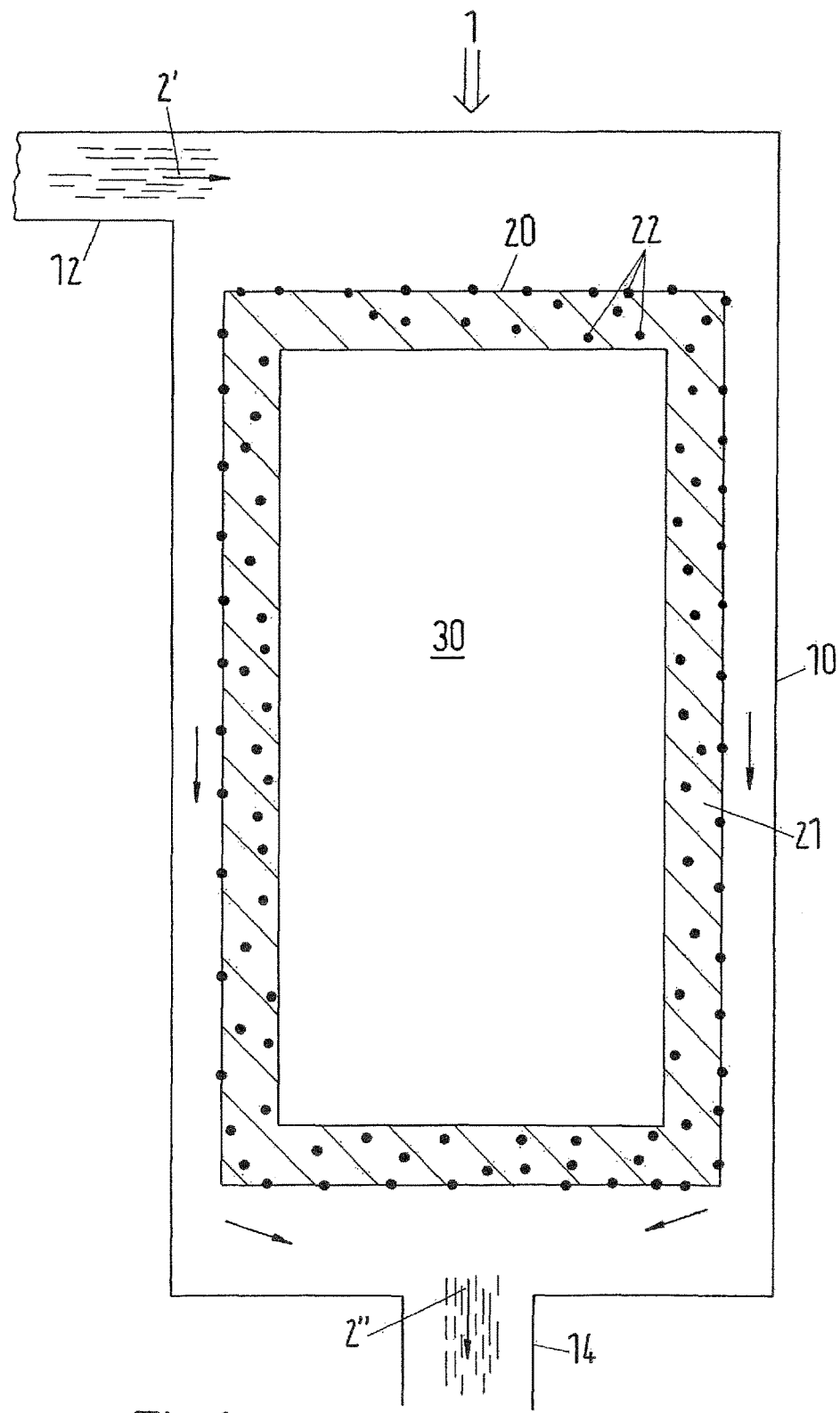
FIG. 1 shows a schematic view of an embodiment of an apparatus for germ reduction of a fluid according to the invention.
Figure 2:
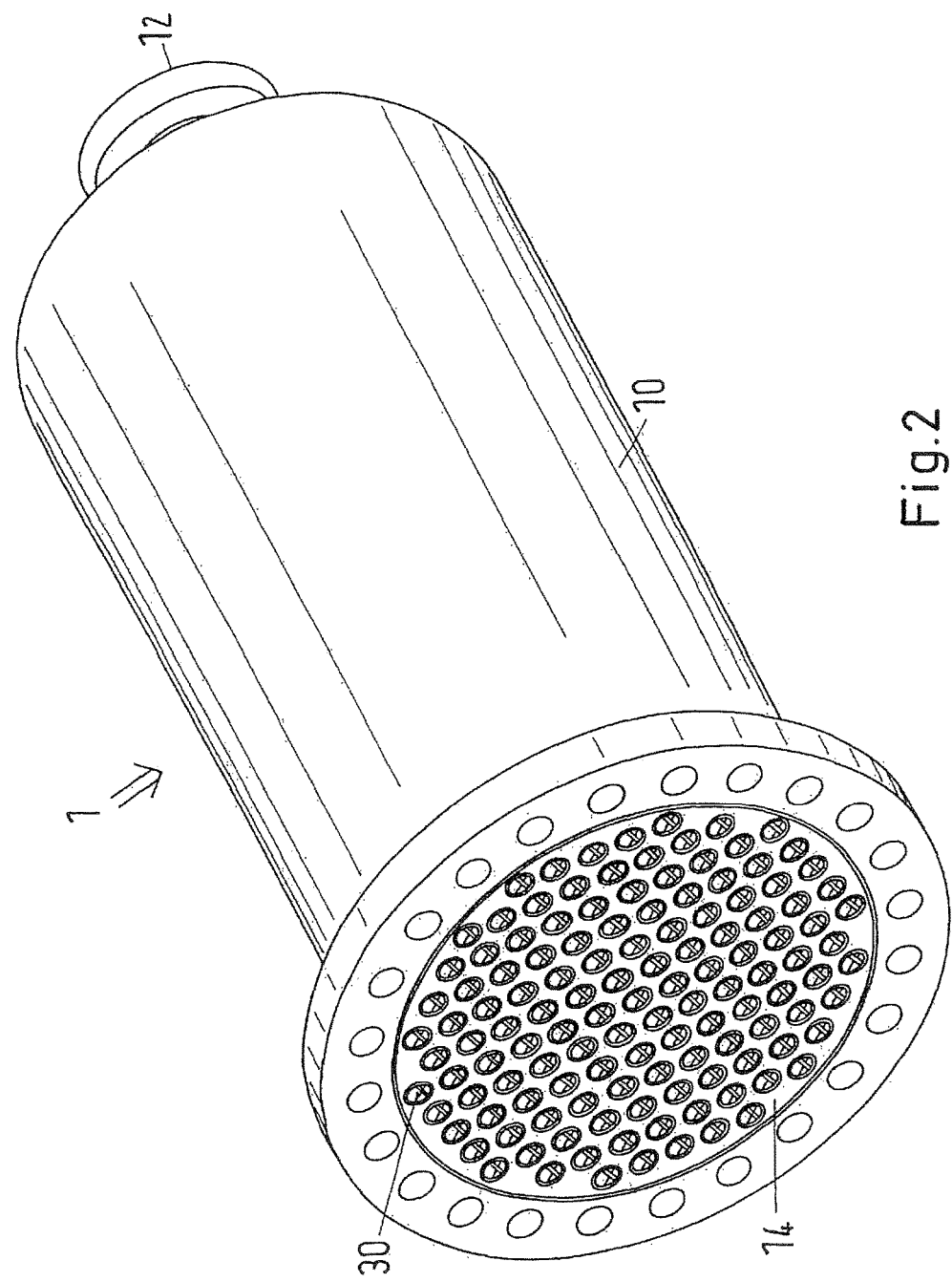
FIG. 2 shows a schematic view of an embodiment of the apparatus of the invention in the form of a multitube apparatus.
Figure 3:
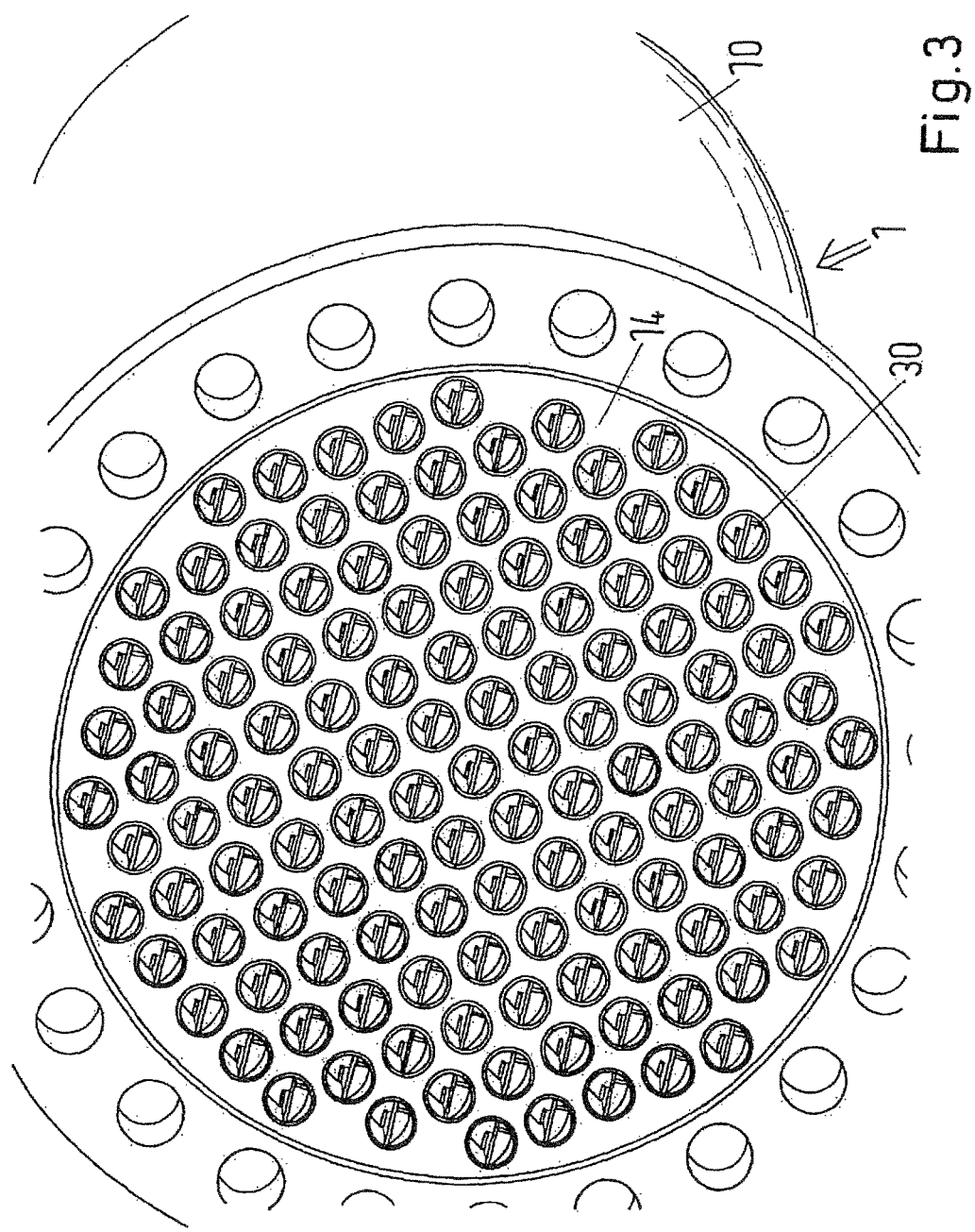
FIG. 3 shows a schematic view of a more specific embodiment of the apparatus of FIG. 2 in which the static mixing elements are helical static mixing elements.
Figure 4:
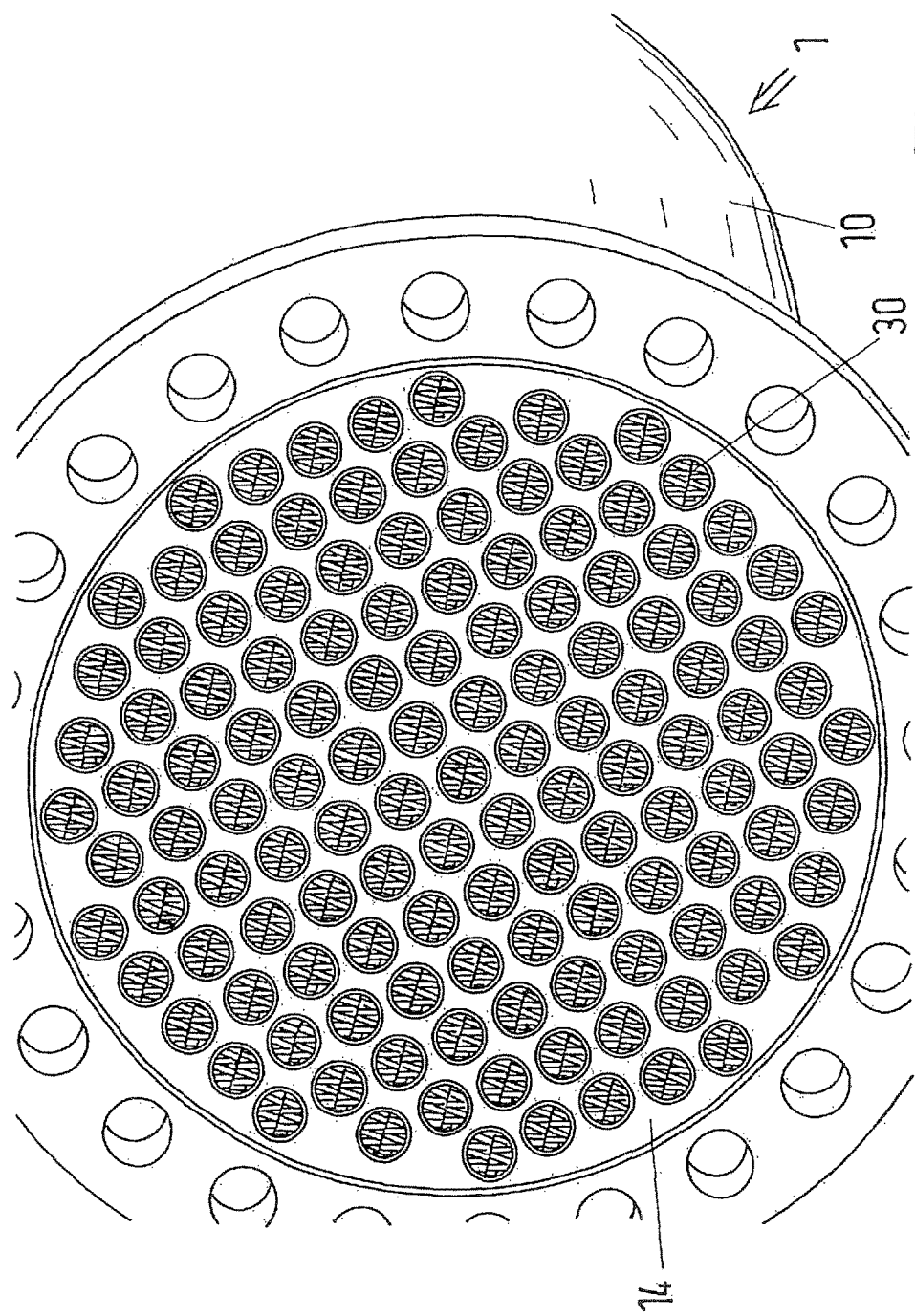
FIG. 4 shows a schematic view of another more specific embodiment of the apparatus of FIG. 2 in which the static mixing elements are crossed web static mixing elements.
Figure 5:
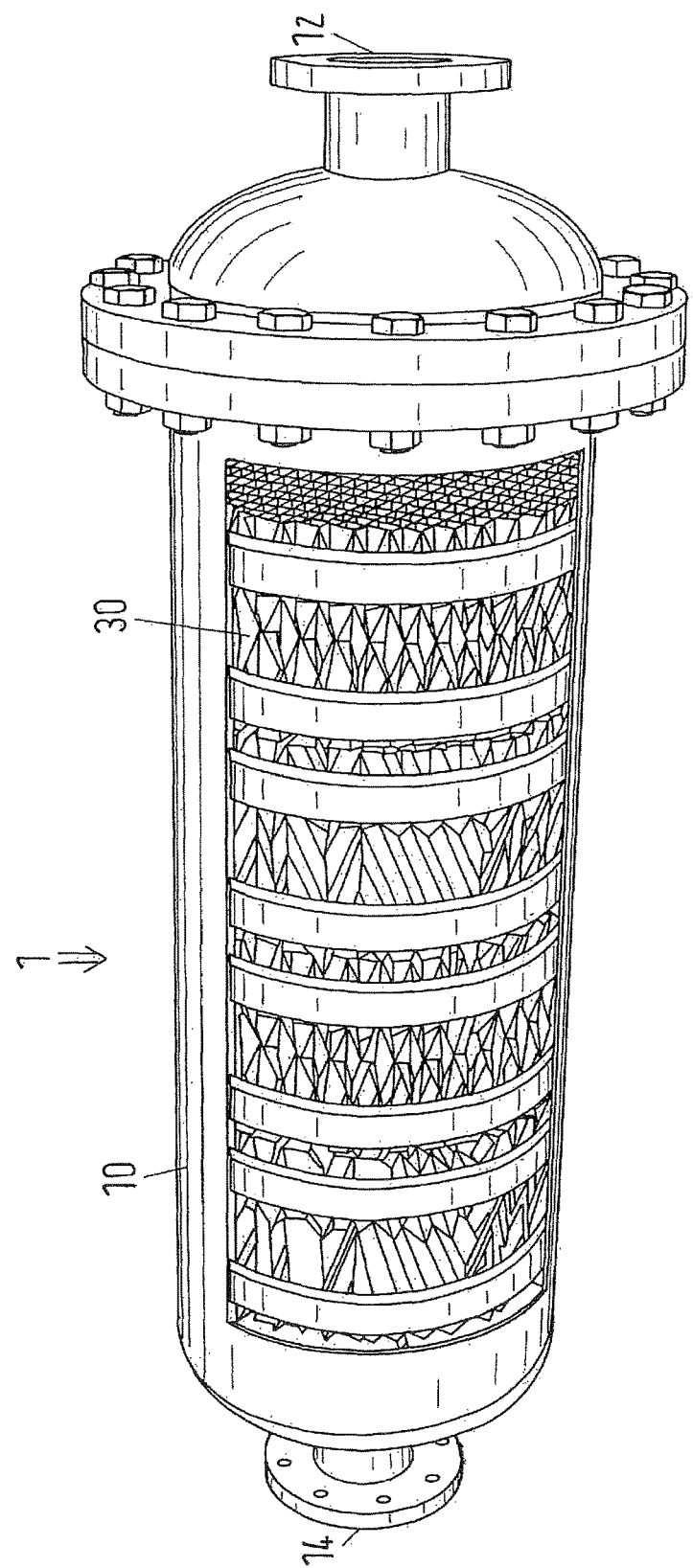
FIG. 5 shows an alternative embodiment of the apparatus of the invention in the form of a column filled with packing elements.

FIG. 1 shows a schematic view of an embodiment of an apparatus for germ reduction of a fluid 2 according to the invention, which as a whole is labeled with reference number 1. The apparatus 1 is not specifically limited as to form, shape, construction or composition unless specifically indicated otherwise. The apparatus 1 comprises:

a housing 10
an inlet 12
an outlet 14
a fluid-contacting surface 20 comprising a biocide 22 embodied to reduce the germ count of the fluid 2,
wherein the fluid-contacting surface 20 is a fluid-contacting surface 20 of a static mixing element 30.

The fluid 2 to be treated is not specifically limited and may be liquid or gas phase, preferably liquid phase. Example fluids 2 include air, water, aqueous solutions, fuel oil, liquid food products, and beverages.

Static mixing elements 30 and static mixers and their construction and operation are well known in the art, for example, as disclosed in Handbook of Industrial Mixing: Science and Practice, edited by E. L. Paul, V. A. Atiemo-Obeng, S. A. Kresta, published by John Wiley and Sons in 2004 (ISBN 0-471-26919-0). Unless specifically indicated otherwise, conventional construction materials and means, as well as components and auxiliaries, may be used for the apparatus 1, and the apparatus 1 may be operated in a static mixing process in a conventional manner using conventional process parameters such as operating temperatures, operating pressures, and residence times as known in the art. For example, these cited reference textbooks disclose a variety of conventional preheaters, distributors, manifolds, internals, pumps, and valves for use with static mixing elements 30 in static mixers and other equipment.

The static mixing element 30 is not specifically limited, and it is generally a baffle, typically helical in shape, contained in the typically cylindrical (tube) or squared housing 10. Suitable static mixer elements 30 will fulfill the function of providing a fluid-contacting surface 20 for enabling a contact between the biocide 22 and the fluid to be treated. In order to fulfill this function, the static mixer element 30 will have a void fraction of greater than 50, preferably 65, more preferably 70%. The void fraction in the present application is defined as the ratio of the free volume available for fluid to the working volume of the apparatus encompassing the static mixer element.

In one embodiment the elements are helical or pseudo-helical and are arranged in a series of alternating left and right hand 180 degree twists. The elements split the fluids entering in two streams and than rotate them through 180 degrees. In another embodiment the static mixer element consists of intersecting corrugated plates and channels that encourage rapid mixing in combination with plug flow progression.

Suitable static mixer design types include the corrugated plate, wall-mounted vanes, cross-bar, and helical twist types. Specific suitable static mixers for use with the invention include the Sulzer Chemtech SMX™ and SMX™ Plus, SMV™ static mixers.

Suitable static mixer elements 30 include those disclosed in GB1373142 (A), U.S. Pat. No. 3,918,688 (A), and GB2061746 (A). In one embodiment, the static mixer element 30 comprises a plurality of layers in contact with one another, each layer bounding flow channels for the fluid, the axes of which are substantially parallel to the corresponding layers, the longitudinal axes of at least two flow channels of each layer being parallel and inclined to the longitudinal axes of at least some of the flow channels of an adjacent layer or layers, and at least some of the flow channels of each layer being arranged to communicate with flow channels of an adjacent layer.

In another embodiment, the static mixer element 30 comprises one mixer element in the form of crossed webs disposed at an angle with a tube axis, the webs being disposed in at least two groups, the webs of any one group of elements extending substantially parallel to one another and the webs of one group crossing the webs of the other group, in which the maximum web width (b) is from 0.1 to 0.167 times the tube diameter (d), the normal between-webs distance (m) in each group is from 0.2 to 0.4 times the tube diameter (d) and the length (l) of the mixer element is from 0.75 to 1.5 times the tube diameter (d).

Generally multiple static mixing elements 30 will be located in series in the housing 10. The necessary number of mixing elements 30 for a specific application will depend on the required homogeneity and contact between the fluid 2 and the fluid-contacting surface 20 comprising a biocide 22. One skilled in the art will understand that factors such as increased germ content of the fluid 2, more extensive required germ reduction, or reduced biocide 22 content in the fluid contacting surface 20 may require a larger number of static mixing elements 30 to be used. The static mixer element 30 in other embodiments may also be in the form of a random or structured packing element. Suitable random packings include Pall rings, Nutter rings, and other structures typically manufactured from thin metal sheets and typically used in mass transfer applications. Suitable structured packings include those under the tradenames Sulzer Mellapak™ or MellapakPlus™ structured packing, and such structured packings are typically manufactured from corrugated metal sheets or wire mesh or gauze and typically used in mass transfer applications.

FIG. 2 shows one embodiment of apparatus 1 comprising a housing 10, an inlet 12, an outlet 14, and static mixing elements 30 contained within a series of parallel tubes, analogous in construction to a multitube heat exchanger. FIGS. 3 and 4 show specific embodiments in which the static mixer elements 30 are in the form of helical static mixing elements (FIG. 3) or in the form of cross webs (FIG. 4).

FIG. 5 shows another embodiment of apparatus 1 comprising a housing 10, an inlet 12, an outlet 14, and static mixing elements 30, analogous in construction to a column filled with packing elements. In the specific embodiment shown in FIG. 5, the packing elements are structured packing elements. In other embodiments, the packing elements may be random packing elements.

Suitable construction materials for the apparatus 1 and its components such as the static mixing element 30 may include plastics, preferably thermoplastics such as PE, PP, PA, PU, or PVDF; or metals such as aluminium, steel, or copper; or ceramics.

The biocide 22 for use in the invention is not specifically limited. In the present application a biocide is defined as a chemical substance which can deter, render harmless, or exert a controlling effect on any harmful organism. Industrial biocides are known in the art, for example, as disclosed in Industrial Biocides: Selection And Application, edited by D. R. Karsa and D. Ashworth, and published by the Royal Society of Chemistry in 2002 (ISBN 0-85404-805-7). Suitable biocides 22 include Polymeric Guanidines, Quaternary Ammonium Compounds, Phenols, Cresols, Alcohols, Aldehydes, Glutaraldehydes, Ethylene Oxide, Organic Acids, Metallic Salts/Ions, Isothiazolinones, Peroxides, Chlorine compounds, Halogens, Anionic-, Amphoteric- and Cationic-agents, Iodophors, Dibromo-derivates, Pentamidines, Propamidines and/or subgroups of the above and/or mixtures of two or more of the above and/or their subgroups. Other biocides and mixtures of two or more of them and/or containing one or more of them may be suitable as well.

Figure 6:
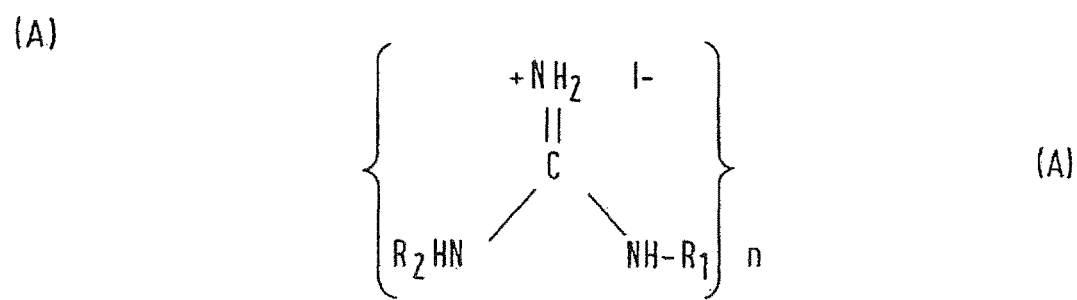
FIG. 6 shows an embodiment of a general formula (A) for polymeric guanidines suitable for use in the present invention.

In some selected embodiments the biocide 22 is in the form of a biocide-containing polymer such as a Surface Active Material (SAM) including polymeric guanidines. FIG. 6 shows the general formula of suitable polymeric guanidines in which R1 and R2=independently of each other H, [—C(=NH)—NHR3], or an aliphatic, cycloaliphatic, aralipatic or aryl organic group, or an acyl group comprising such an organic group; R3=H or an aliphatic, cycloaliphatic, aralipatic or aryl organic group, or an acyl group comprising such an organic group; I—=anion and n≥2. Suitable polymeric guanidines include those disclosed in "Biocide guanidine containing polymers, Synthesis, structure and properties", by N. A. Sivov, in New Concepts In Polymer Science, VSP Publications Leiden 2006 (ISBN-13: 978-9067644471).

Suitable biocide-containing copolymers for use in the invention include polyurethanes and/or polycarbamides with polymeric guanidines as a comonomer (as disclosed in EP 2338342A1 and/or EP2338923A1) and/or quaternized polyurethanes.

In certain more specific selected embodiments the biocide 22 is contained in a polymer compound. Polymers suitable for making such compounds of biocides are not specifically limited. In a preferred embodiment, the polymers include Polyurethane, Polyethylene, Polypropylene, Polyamide, Polyvinylidenfluoride, Polyester, Polyether, Polytetrafluorethylene, Silicone, Polyvinylchloride, and Polycarbamide. Other suitable polymers include Polyethyleneterephthalate, Polybutyleneterephthalate, Polystyrol, Polyphenylenesulfide, Polyacrylnitrile, Polyimide, Silane, Epoxide, Rubber, Acrylnitril-Butadien-Styrol, Duroplasts, Aminoplasts, Melamine, Aramide, Polyamidimide, Polyacrylonitriles, Polymethacrylnitrile, polyacrylamides, polyimides, polyphenylene, polysilanes, polysiloxanes; polybenzimidazoles; polybenzothiazoles; polyoxazoles; polysulfides; polyarylene vinylene; polyetherketone; polyetheretherketone; polysulfones, inorganic-organic hybrid polymers; fully aromatic copolyesters, poly(alkyl)acrylates, poly(alkyl)methacrylates; polyhydroxyethylmethacrylates; polyvinyl acetates, polyvinyl butyrates, polyisoprene, synthetic rubbers; modified and unmodified cellulosics, homo- and copolymers of alpha-olefins, polyvinyl alcohols, polyalkylene oxides, polyethylene oxides, polyethylene imides, poly-N-vinylpyrrolidones; fully aromatic copolyesters, poly(alkyl)acrylates, poly(alkyl)methacrylates; polyhydroxyethylmethacrylates; polyvinyl acetates, polyvinyl butyrates, polyisoprene, synthetic rubbers; modified and unmodified cellulosics, homo- and copolymers of alpha-olefins, polyvinyl alcohols, polyalkylene oxides, polyethylene oxides, polyethylene imides, poly-N-vinylpyrrolidones; and mixtures of two or more of the above. Other polymers and/or plastics and mixtures of two or more of them and/or containing one or more of them may be suitable as well.

Biocides 22 suitable for compounding into polymers include those disclosed above. Suitable polymer compounds for use in the present invention include those disclosed in EP2338923A1 and EP2338342A1. Suitable polymers for compounding include the above disclosed polymers. Preferred polymer compounds include PE and/or PP and/or PA and/or PVDF and/or PU and/or polycarbamides with Polymeric Guanidines and/or Quaternary Ammonium Compounds and/or metallic salts/ions and/or Isothiazolinones and/or Aldehydes and/or phenols. More preferred polymer compounds include PE and/or PP and/or PA and/or PVDF and/or PU and/or polycarbamides with Polymeric Guanidines, and most preferred are polymer compounds are PA and/or PU with Polymeric Guanidines.

In certain embodiments such as that shown schematically in FIG. 1 the static mixing element 30 contains biocide 22 only in a surface region 21 encompassing the fluid-contacting surface 20. Preparing such static mixing elements 30 may be done by a variety of conventional thermal or solution processing methods such as laminating, extruding, dip coating, spray coating, or vapor deposition. Suitable coating processes are disclosed for example in the BASF Handbook on Basics Of Coating Technology, by A. Goldschmidt and H.-J. Streitberger, published by Vincentz Network in 2003 (ISBN 3-87870-798-3).

In the case of coatings, the static mixer element 30 will often comprise a primer layer underneath the surface region 21 in order to increase the strength of the bonding and permanence of the coating on the coated static mixer element 30'. Suitable chemical primers for metals such as steels or aluminum for use in the invention include zinc phosphate, iron phosphate, alkyd resins, 2K Epoxy-Zinc phosphate, Silanes, and 2K Epoxy resin. Suitable coatings for use in the invention include 2K or 1K solutions such as chlorinated rubbers, rubbers, nitrocellulosics, polyesters, phenolic resins, urea and melamine resins, epoxy resins, epoxy-silanes, acrylic resins and fluoropolymers. Preferred coatings include chlorinated rubbers, epoxy resins, fluoropolymers and epoxy-silanes, and rubbers. Specific embodiments of coating agents include fluoropolymers.

For the case of coatings, typical thicknesses of the surface region 21 will be from 10 to 150 μm. One skilled in art will understand that thicker surface regions 21 are better if there are stresses or a required longer lifetime in the application. One skilled in the art will understand that different coating methods will typically result in different thicknesses.

Auxiliaries for the apparatus 1 are conventional and well-known in the art and may include electrical supplies, coolant and heating fluid supplies and distributions, level controllers, pumps, valves, pipes and lines, reservoirs, drums, tanks, and sensors for measuring such parameters as flow, temperatures and levels. The apparatus 1 and the process of the invention may be conveniently controlled by means of a computer interface equipped with appropriate sensors.

Although not shown in the schematic figures for simplicity, one skilled in the art will understand that other conventional apparatus internals may be used without limitation in the invention, such as feed devices like feed pipes and/or sumps, heat exchangers, support plates and grids, dispersers, disperser/support plates, continuous phase distributors, support and hold-down plates, baffles, deflectors, entrainment separators, and retainers/redistributors.

Another aspect of the invention is a process for reducing the germ count of a fluid containing germs 2' using an apparatus 1 of the invention. Such a process is illustrated schematically in FIG. 1. The fluid containing germs 2' is fed to the apparatus 1 via the inlet 12, and then the fluid containing germs 2' is treated on a fluid-contacting surface comprising a biocide 22 in order to form a fluid having a reduced germ count 2". The fluid having a reduced germ count 2" is subsequently removing from the apparatus 1 via the outlet 14. The flows of the fluids, 2' and 2", through the apparatus 1 are schematically illustrated by the use of arrows in FIG. 1.

Processes for germ reduction in fluids are well known in the art, for example, as disclosed in the earlier cited reference books, as well as in Disinfection, Sterilization, and Preservation, edited by S. S. Block, published by Lippincott Williams and Wilkins as the 5$^{th}$ edition in 2001 (ISBN 0-683-30740-1). Unless indicated otherwise, the various fluid feed streams and operating parameters and conditions of such conventional types of germ reduction processes may be generally used here in the germ reduction process according to the invention and making use of the apparatus 1. In addition, in specific embodiments the apparatus of the invention may be used alone or together with gem reduction apparatuses known in the art. In one embodiment, the apparatus of the invention will be used together with ultraviolet germ reduction devices such as HF-excited gas discharge lamp.

EXAMPLES

The following examples are set forth to provide those of ordinary skill in the art with a detailed description of how the apparatus 1 for germ reduction of a fluid 2, processes for reducing the germ count of a fluid containing germs 2', and uses claimed herein are evaluated, and they are not intended to limit the scope of what the inventors regard as their invention.

In these examples, the apparatus 1 and process of the invention were successfully used in a typical application for the reduction of germ count of a water sample containing *E. coli* with a germ count which greatly exceeds the germ count commonly found in the foreseen application areas for the invented apparatus, namely between about $7\times10^7$ to $7\times10^8$ cells per mL.

In working examples Sulzer SMV™ DN15 static mixing elements 30 were coated with biocide-containing polymer in the form of the following polymer compounds: polyamide (PA), polyethylene (PE), fluoropolymer, or polyurethane (PU) compounded with a guanidine or a derivative thereof as a biocide 22. The coating was carried out in a dip coating process in which the static mixing elements 30 were first placed in a coating bath for 10 s. After their removal from the bath, the solvent was evaporated and the coating was hardened by treating the static mixing elements 30 for 2 hours at room temperature, followed by 2 h at 65° C., and then 8 h at room temperature, followed by 1 h at 65° C. The resulting static mixing elements 30 thus had fluid-contacting surfaces 20 comprising a biocide 22. Apparatuses 1 were then constructed using a housing 10 in the form of a silicone tube containing a total of 5 of the biocide-coated static mixing elements 30.

As comparative examples, granulates having diameters of either 3 or 5 mm and comprising the same biocide-containing polymers were tested by constructing a packed bed of the biocide-containing granulates in a silicone tube housing. The packed beds were constructed so as to have similar active biocide-containing surface areas as in the apparatuses 1 of the above working examples.

Comparative tests of the germ count reduction properties of the apparatuses 1 of the working examples of the invention versus the packed beds of the prior were carried out under both static and dynamic conditions. "Blank" control examples were also run using apparatuses constructed using static mixing elements that had not been coated with the biocide-containing polymer. The treated fluids in the working and comparative examples were analyzed for germ count using proliferation assays based on the commonly used ISO germ count methodology.

Figure 7:
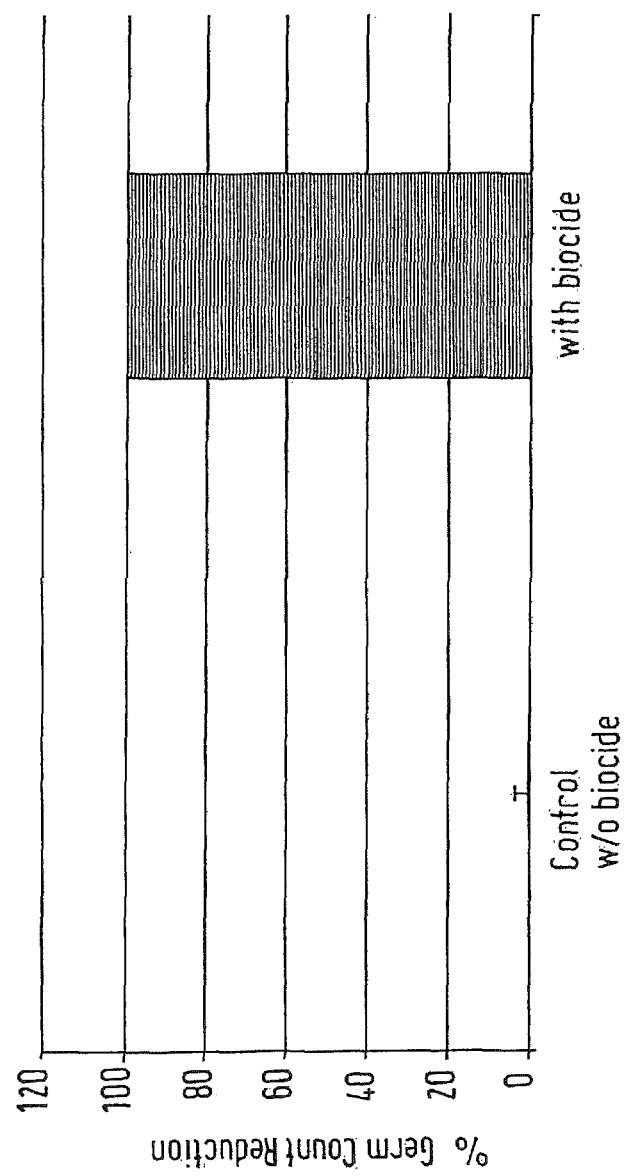
FIG. 7 shows example data for the reduction in germ count obtained by an embodiment of the apparatus of the invention in a process having a residence time of 5 s.

FIG. 7 shows representative results for the germ count reduction in a dynamic test of an embodiment of the apparatus 1 of the invention (coated static mixing elements) versus a control apparatus (uncoated static mixing elements). After a residence time of only 5 s the reduction in germ count is on the order of at least $5\times10^5$ in the case of the coated static mixing elements 30 coated with biocide-containing polymers, and no active germs could be detected. In the case of the blank control apparatus having uncoated static mixers, no reduction in the germ count could be detected.

Figure 8:
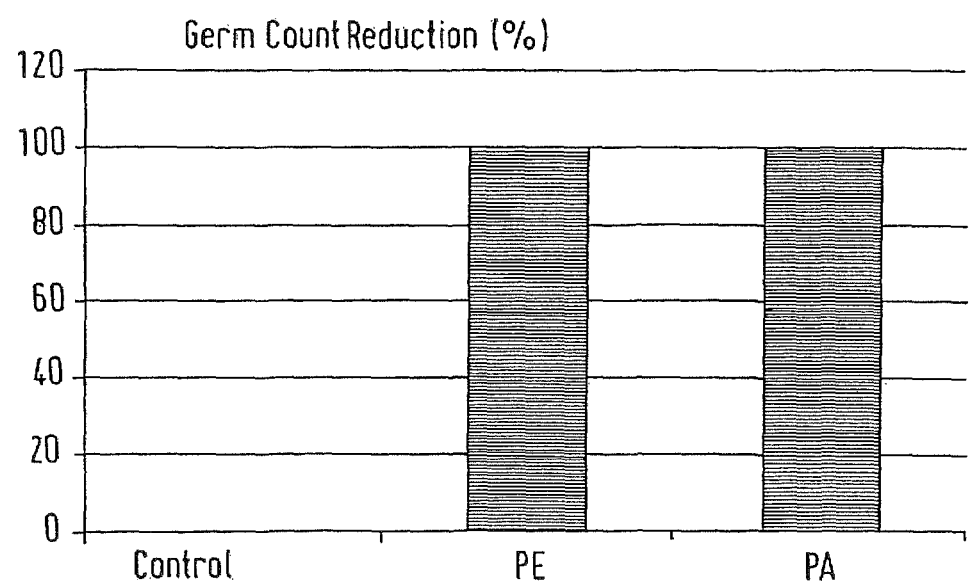
FIG. 8 shows example data for the reduction in germ count obtained by other embodiments of the apparatus of the invention in a process having a residence time of 10 s.

FIG. 8 shows representative results for the germ count reduction in a dynamic test of an embodiment of the apparatus 1 of the invention (coated static mixing elements) versus a control apparatus (uncoated static mixing elements). The coated static mixing elements 30 were coated with polymer compounds based on either PE or PA and containing biocide in the working examples, and 10 s residence times were used in these dynamic tests. As in the case of the earlier examples, the germ count was essentially undetectable after 10 s in the case of the working examples, whereas it was essentially unchanged in the control test using uncoated static mixing elements.

In the comparative examples based on the granulate beds, not only were the pressure losses significantly higher than those in the above working examples based on embodiments of the apparatuses 1 of the invention, but also the germ reduction was generally much poorer in the case of the packed beds of granulate than in the case of the working examples having similar active biocide-containing surface areas.

Figure 9:
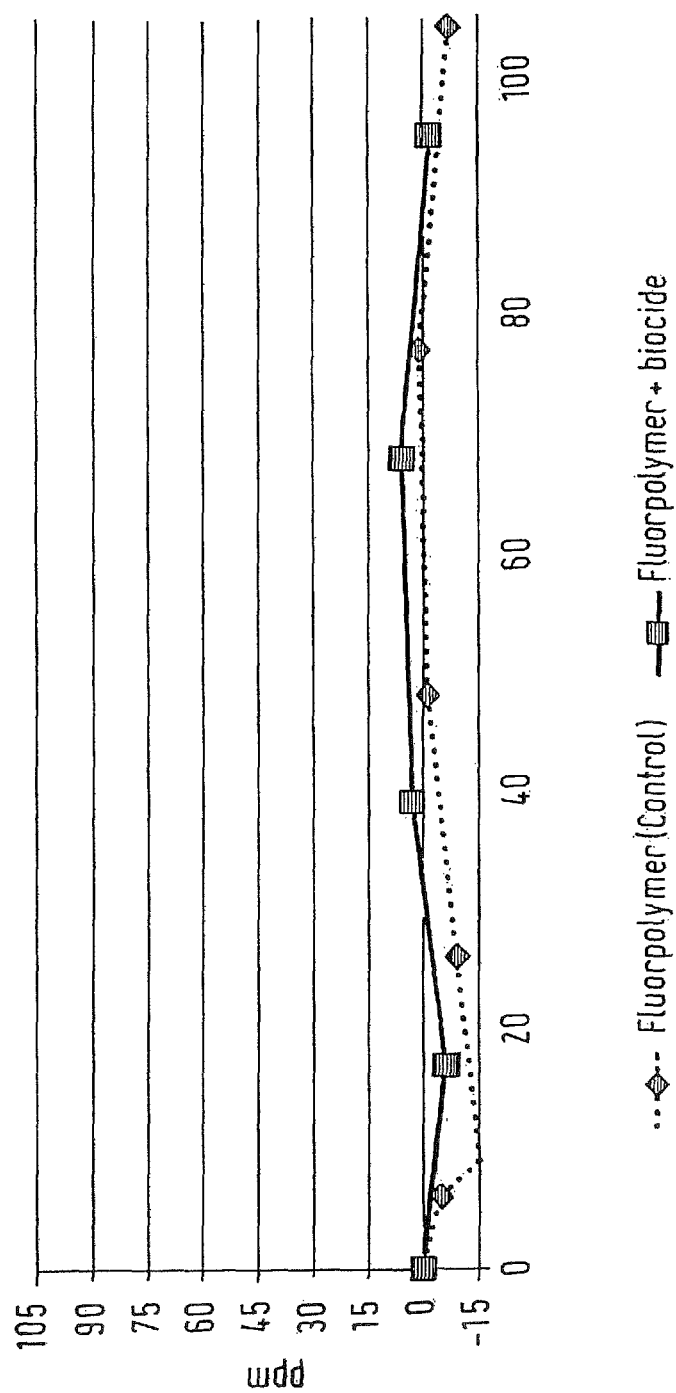
FIG. 9 shows the favourable stability against migration of the biocide out of an embodiment of a static mixing element coated with a fluoropolymer-based compound of the biocide

FIG. 9 shows the long-term testing of stability against migration of the biocide out of model static mixing elements 30 based on aluminum coated with fluoropolymer compounds of the biocide. Under static conditions in water at 37° C. over 95 days, no biocide was detectable in the surrounding water by means of spectroscopic analysis in the case of either the static mixing elements 30 coated with the fluoropolymer compound or the uncoated blank control samples.

While various embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. An apparatus for germ reduction of a fluid comprising:
   a housing;
   an inlet;
   an outlet; and
   a fluid-contacting surface comprising a biocide embodied to reduce the germ count of the fluid; wherein the fluid-contacting surface is a fluid-contacting surface of a static mixing element, and wherein the fluid-contacting surface comprises a guanidine or a derivative thereof being selected from the group consisting of:
(i) a polymeric guanidine according to the general formula

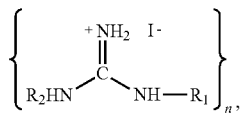

wherein R1 and R2 are independently of each other H, [—C(=NH)—NHR3], or an aliphatic, cycloaliphatic, araliphatic or aryl organic group, or an acyl group comprising such an organic group; R3 is H or an aliphatic, cycloaliphatic, araliphatic or aryl organic group, or an acyl group comprising such an organic group; and I— is anion and n greater than or equal to two;
(ii) a polymer compound selected from the group consisting of polyethylene, propylene, polyamide, PVDF, polyurethane, and polycarbamides compounded with the polymeric guanidine described above; and
(iii) a polymer compound selected from the group consisting of polyamide, polyethylene, fluoropolymer, and polyurethane compounded with guanidine or a derivative thereof wherein the fluid-contacting surface does not substantially release the biocide to the fluid such that the concentration of biocide in a fluid contacting the fluid-contacting surface is less than 50 ppm.

2. The apparatus of claim 1, wherein the fluid-contacting surface comprises a biocide-containing polymer.

3. The apparatus of claim 2, wherein the biocide-containing polymer is a copolymer.

4. The apparatus of claim 3, wherein the static mixer element contains biocide only in a surface region encompassing the fluid-contacting surface.

5. The apparatus of claim 2, wherein the biocide-containing polymer is a polymer compound.

6. The apparatus of claim 1, wherein the static mixer element contains biocide only in a surface region encompassing the fluid-contacting surface.

7. A process reducing the germ count of a fluid containing germs using the apparatus of claim 1, the process comprising the steps of:
feeding the fluid containing germs to the apparatus via the inlet,
treating the fluid containing germs on the fluid-contacting surface comprising a biocide in order to form a fluid having a reduced germ count,
removing the fluid having a reduced germ count from the apparatus via the outlet.

8. The process of claim 7, wherein a residence time in the apparatus is less than 600 s.

9. The process of claim 7, wherein a temperature of the fluid in the apparatus is between 0 and 200° C.

10. The process of claim 7, wherein a germ count of the fluid is reduced in the process by log 0.5 to 7.

11. The process of claim 7, wherein a pressure of the fluid in the process is less than or equal to 100 bar.

12. The process of claim 7, wherein a ratio of an active surface to a volume of the apparatus is more than 50 m2/m3.

13. The process of claim 7, wherein a viscosity of the fluid in the process is less than 1000 Pa s.

14. The process of claim 7, wherein a pressure loss of the fluid is less than 1 bar.

15. A method for use of the apparatus of claim 1 comprising the steps of
providing the apparatus of claim 1 and
using it in a process of germ reduction of fuel oil, of food products, or water decontamination by introducing a fluid to the inlet.

16. The apparatus of claim 1, wherein the fluid-contacting surface does not substantially release the biocide to the fluid such that the concentration of biocide in a fluid contacting the fluid-contacting surface is less than 15 ppm.

17. The apparatus of claim 1, wherein the fluid-contacting surface does not substantially release the biocide to the fluid such that there is no detectable level of biocide in a fluid contacting the fluid-contacting surface.

18. The apparatus of claim 1, wherein the wherein the fluid-contacting surface is a liquid contacting surface that does not substantially release the biocide to the liquid such that the concentration of biocide in a liquid contacting the fluid-contacting surface is less than 50 ppm.

19. An apparatus for germ reduction of a fluid comprising:
a housing;
an inlet;
an outlet; and
a fluid-contacting surface comprising a biocide embodied to reduce the germ count of the fluid; wherein the fluid-contacting surface is a fluid-contacting surface of a static mixing element, and wherein the fluid-contacting surface comprises a guanidine or a derivative thereof being selected from the group consisting of:
(i) a polymeric guanidine according to the general formula

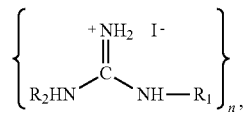

wherein R1 and R2 are independently of each other H, [—C(=NH)—NHR3], or an aliphatic, cycloaliphatic, araliphatic or aryl organic group, or an acyl group comprising such an organic group; R3 is H or an aliphatic, cycloaliphatic, araliphatic or aryl organic group, or an acyl group comprising such an organic group; and I— is anion and n greater than or equal to two;
(ii) a polymer compound selected from the group consisting of polyethylene, propylene, polyamide, PVDF, polyurethane, and polycarbamides compounded with the polymeric guanidine described above; and
(iii) a polymer compound selected from the group consisting of polyamide, polyethylene, fluoropolymer, and polyurethane compounded with guanidine or a derivative thereof wherein the fluid-contacting surface does not substantially release the biocide to the fluid such that the concentration of biocide in a fluid contacting the fluid-contacting surface is less than 50 ppm, and
wherein the static mixer element comprises a plurality of layers in contact with one another, each layer bounding flow channels for the fluid, the axes of which are substantially parallel to the corresponding layers, the longitudinal axes of at least two flow channels of each layer being parallel and inclined to the longitudinal axes of at least some of the flow channels of an adjacent layer or layers, and at least some of the flow channels of each layer being arranged to communicate with flow channels of an adjacent layer or the static mixer element comprises one mixer element in the form of crossed webs disposed at an angle with a tube axis, the webs being disposed in at least two groups, the webs of any one group of elements extending substantially parallel to one another and the webs of one group crossing the webs of the other group.

* * * * *